United States Patent [19]

Armentrout et al.

[11] Patent Number: 4,464,471

[45] Date of Patent: Aug. 7, 1984

[54] BIOLOGICALLY ENGINEERED PLASMID CODING FOR PRODUCTION OF β-GLUCOSIDASE, ORGANISMS MODIFIED BY THIS PLASMID AND METHODS OF USE

[75] Inventors: Richard W. Armentrout; Ronald D. Brown, both of Cincinnati, Ohio

[73] Assignee: University of Cincinnati, Cincinnati, Ohio

[21] Appl. No.: 344,298

[22] Filed: Feb. 1, 1982

[51] Int. Cl.$^3$ .................... C12N 1/20; C12N 15/00; C12N 9/38; C12N 9/42; C12N 1/00; C12N 9/00; C12P 7/06; C12P 7/10; C12P 21/00; C12R 1/185; C07H 21/04

[52] U.S. Cl. .................... 435/253; 435/161; 435/165; 435/68; 435/172; 435/207; 435/209; 435/317; 435/848; 435/183; 536/27

[58] Field of Search ............ 435/161, 172, 253, 207, 435/209, 848, 317, 183, 163, 165, 68; 536/27

[56] References Cited

U.S. PATENT DOCUMENTS

| | | | |
|---|---|---|---|
| 3,990,944 | 11/1976 | Gauss et al. | 435/165 |
| 4,009,075 | 2/1977 | Hoge | 435/162 |
| 4,094,742 | 6/1978 | Bellamy | 435/42 |
| 4,220,721 | 9/1980 | Emert et al. | 435/163 |
| 4,224,410 | 9/1980 | Pemberton et al. | 435/162 |
| 4,275,163 | 6/1981 | Gallo | 435/172 |

FOREIGN PATENT DOCUMENTS 2055121 2/1981 United Kingdom ............ 435/161

OTHER PUBLICATIONS

Helling et al.; in *Genetic Engineering*, Chakrabarty (ed.), CRC Press, 1978, pp. 1–30.

*Primary Examiner*—Thomas G. Wiseman
*Assistant Examiner*—James Martinell

[57] ABSTRACT

A biologically engineered plasmid coding for the production of β-glucosidase. The plasmid can be incorporated into various microorganisms to enable the microorganism to digest cellobiose, which is produced from cellulose by an endo- or exocellular cellulase. One particular application is the incorporation of this plasmid into a microorganism which produces ethanol. Preferably, this ethanol producing microorganism is also ethanol tolerant.

2 Claims, No Drawings

BIOLOGICALLY ENGINEERED PLASMID CODING FOR PRODUCTION OF β-GLUCOSIDASE, ORGANISMS MODIFIED BY THIS PLASMID AND METHODS OF USE

Microorganisms have for years played an extremely important function in the production of various chemicals, pharmaceuticals and other natural products. One example of such use has been the fermentation of grains to produce alcohol. Microorganisms require a source of carbon. There are various sources of carbon for different organisms such as starches, sugars including cellulose, and other compounds such as alcohols.

Typically, microorganisms are specific in that they cannot indiscriminately use any carbon source. Many organisms which can feed on simple sugars such as sucrose cannot feed and grow on cellulose. When these microorganisms are used for industrial purposes, it is desirable to use as inexpensive a carbon source as possible. Cellulose is extremely inexpensive compared to sucrose, fructose, glucose and other simple sugars. Some organisms are known which do break down cellulose, but for various reasons are unsuitable for a particular industrial application. For example, there are no known microorganisms which utilize cellulose and produce ethanol and which are ethanol tolerant.

Microorganisms have been employed to produce ethanol from cellulose. For example, Gauss et al U.S. Pat. No. 3,990,944 discloses digesting cellulose with a separately prepared cellulase to form glucose and using a microorganism to produce ethanol from the formed glucose. One of the most promising recent developments has been in the study of anaerobic bacteria capable of direct fermentation of cellulose to ethanol. *Clostridium thermocellum* has been the subject of much recent study. This bacterium digests cellulose and produces ethanol without the necessity for separate enzyme production processes and does not require expensive nitrogen sources. Fermentation proceeds at a high temperature which improves the rate of the process and might decrease the distillation costs. Unfortunately, the bacteria has very poor ethanol tolerance and even improved strains do not continue fermentation once the level of ethanol passes 2%. In addition, the tolerance appears to decline as the temperature increases. Ethanol tolerance is a complex problem which does not appear to have any simple solution. Again, there are theoretical means of overcoming this problem including some form of continuous fermentation with simultaneous removal of ethanol. These solutions may be quite expensive and fairly complex in terms of the necessary equipment. None of these microorganisms have been modified using recombinant DNA technology.

Today genetic engineering is used to create new microorganisms. For example, Chakrabarty U.S. Pat. No. 4,259,444 discloses the method of producing a new microorganism which includes inserted recombinant DNA. These microorganisms have multiple, compatible degradative energy-generating plasmids. Cohen et al U.S. Pat. No. 4,237,224 discloses a method of taking specific genetic material, combining it with additional DNA material to form a plasmid, and inserting this plasmid into a microorganism by transformation. This method is now well known and has been used to create many new microorganisms.

Until now, no one has attempted to utilize this recombinant DNA technology to modify a microorganism by transferring the ability to utilize cellulose or cellobiose as a carbon source. Furthermore, this technology has not been used to modify a microorganism to improve its ability to generate ethanol. Particularly, no one has used the recombinant DNA technology to modify a microorganism to incorporate within that microorganism the ability to utilize cellulose as a carbon source and produce ethanol.

The present invention is a recombinant plasmid which codes for the production of β-glucosidase, the enzyme that breaks down cellobiose to glucose. Further, the present invention comprises microorganisms modified by transformation of this plasmid and optionally, transformation of additional genetic material coding for the production of cellulase. If this modified microorganism is capable of producing ethanol, the modified microorganism will be capable of producing ethanol from cellulose.

It is surprising that recombinant DNA technology could be used to transmit the ability to digest cellulose. Enzymatic breakdown of cellulose is complicated. Fungal and bacterial cellulases appear to degrade cellulose primarily to cellobiose. Cellobiose in turn is converted to glucose by β-glucosidase which in most cases is tightly cell-associated. Accordingly, the utilization of cellulose by a microorganism requires the ability to break down cellulose and utilize cellobiose. Previously, it was thought that β-glucosidase activity was extremely complex and, accordingly, would not lend itself easily to genetic engineering processes which would enable the transfer of the genetic coding for the production of β-glucosidase from one microorganism to another.

This invention is predicated in part upon determination that the genetic material which codes for the production of β-glucosidase can be isolated and formed in a substantially pure composition. Further, this genetic material can be transferred from one microorganism to another. These discoveries provide substantial advantages in many areas of utility. For instance, the genetic material can be transferred to an organism unable to digest cellobiose and the organism can be accordingly grown on a cellobiose medium in place of sucrose. This modified organism can be further modified by the addition of genetic material coding for the production of cellulase and, thus the organism could be grown directly on cellulose. Or, in the alternative, a separate source of cellulase, such as fungal produced cellulase, can be added to a solution of cellulose, thereby producing cellobiose upon which the organism can then feed.

This invention may be understood with reference to a specific example of the use of this invention dealing with the production of alcohol from cellulose. In this example, the genetic material coding for the production of β-glucosidase is transmitted to an organism which produces alcohol and which is alcohol-tolerant, such as the organism *Zymomonas mobilis*. *Zymomonas mobilis* exhibits excellent alcohol production abilities as well as alcohol tolerance exeeding 6% and up to 16% alcohol. Therefore, the modified Zymomonas can be used to produce alcohol using cellobiose as a carbon source. If an extracellular cellulase is added, cellulose can be a carbon source. This would alleviate the need for simpler and more expensive sugars. However, if certain of these simpler sugars are present, this Zymomonas can also use these as a carbon source. The Zymomonas can be further modified by addition of a plasmid coding for the generation of an endocellulase. Thus, the modified Zymomonas could produce alcohol from wood in high quantities and without the need for any additional source of cellulase to produce the cellobiose.

A plasmid coding for the production of β-glucosidase could be used in various other functions in addition to the production of alcohol from wood. For example, *Esherichia coli* is presently unable to utilize cellobiose. However, *Esherichia coli* is particularly useful in the production of various chemicals, particularly, interferon. With the present invention, the interferon-producing *Esherichia coli* could be modified so as to use cellobiose as a carbon source, thereby decreasing the cost of the production of the interferon.

DETAILED DESCRIPTION OF THE INVENTION

The plasmid having genetic material coding for the production of β-glucosidase was formed according to the following method. *Esherichia adecarboxylata* is known to naturally utilize cellobiose directly rather than glucose. Accordingly, this bacteria was chosen as a source of genetic material to isolate and subsequently transfer to other bacteria which do not include the cellobiose degradation ability.

*Esherichia adecarboxylata* (*Enterobacter agglomerans*, ATCC 23216) was obtained from the American type culture collection. The bacteria was grown in minimal broth culture containing M-9 salts (1.0 g $NH_4Cl$, 3.0 g $KH_2PO_4$, 6.0 g $NA_2HPO_4$ per liter), 0.5% Casamino acids, 1 μg/ml thiamine and 0.5% cellobiose.

*E. adecarboxylata* was grown to stationary phase on L-Broth (1 liter). The cells were collected by centrifugation, washed once in 100 ml of SET(0.15 M NaCl, 0.001 M EDTA, 0.01 M Tris, pH 7.5) and resuspended in 100 ml of SET with 0.1 M EDTA and 3% SDS (sodium dodecylsulfate). The suspension was heated for 15 minutes at 60° C. The lysate was extracted with an equal volume of phenol-chloroform (1:1) at 4° overnight with gentle shaking. The aqueous layer was removed after centrifugation and precipitated in two volumes of ethanol. The nucleic acid was pelleted by centrifugation and resuspended in double strength SET (20 ml) containing 0.01 M EDTA. RNA was removed by digestion with RNase (1 mg/ml boiled in SET for 10 minutes before use) for 2 hours at 37°. The digestion was terminated by addition of SDS to 1%. The solution was extracted with phenol three times and once with ether. The resulting aqueous DNA solution was extensively dialyzed against SET. Thirty micrograms of the purified *E. adecarboxylata* DNA was digested with 30 units of restriction enzyme Eco RI for 1 hour at 37°. The reaction was stopped by addition of diethylpyrocarbonate (0.1%), and incubation at 37° for 10 minutes was followed by desiccation.

Plasmid DNA was isolated from chromosomal DNA by the preferential precipitation of the higher molecular weight chromosomal DNA in the presence of sodium lauryl sulphate. This method is discussed by Guerry et al, (1973) *A General Method For The Isolation of Plasmid Deoxyribonucleic Acid*, J. Bact., 116, 1064, which is incorporated herein by reference as an indication of the level of skill in the art.

A cloning vector pBR322 was used to transfer the *E. adecarboxylata* RI cut DNA into *E. coli*. A cloning vector is a very small derivative of a plasmid which only carries genes necessary for replication and preferably, another gene to serve as a marker such as resistance to a specific antibiotic. Cloning vectors other than pBR322 can be used if desired. Cloning vectors are chosen for various reasons depending on requirements of the situation. These cloning vectors are well known to those of ordinary skill in the art. pBR322 carries the genes for ampicillin and tetracycline resistance. Purified plasmid pBR322 DNA (20 μg was digested with Eco RI (20 units) for 1 hour at 37°. Bacterial alkaline phosphatase (BAP, 18 units) was then added to remove 5' phosphate groups from the ends of the DNA. After digestion for 10 minutes at 37°, the reaction was terminated by addition of SDS (1%) and an equal volume of SET. The DNA was extracted with an equal volume of phenol and the aqueous phase passed over a G-100 Sephadex column (0.1 M NaCl, 0.01 M Tris [pH 7.4], 0.001 M EDTA). The excluded fractions were ethanol precipitated and redissolved in water.

The Eco RI cut and BAP treated pBR322 DNA (1 μg) was mixed with 3 μg of RI cut *E. adecarboxylata* DNA in buffer solution (0.09 M Tris, pH 8.1, 0.035 M $MgCl_2$, 0.05 M dithiothrietol, 0.25 mM ATP) and incubated at 4° C. for 18 hours with $T_4$ ligase (10 units). This ligated DNA was isolated and transferred to *Esherichia coli* strain HB101 ($R^-_G$ $M_b^-$ $F^-$ $Pro^-$ $Thia^-$ $Gal^-$ $Str^R$ $Rec^-$). This strain was grown on minimal broth containing M-9 salts (1.0 g $NH_4Cl$, 3.0 g $KH_2PO_4$, 6.0 g $Na_2HPO_4$ per liter), 0.5 casamino acids, 1 microgram per milliliter thiamine and 0.5% glucose. L broth medium contained 1% bactotryptone (Difco), 0.5% yeast extract, and 0.5% sodium chloride and 0.1% glucose.

The transformation was conducted by treating the cells with a salt solution and subsequently subjecting these cells to heat pulse. More particularly, the concentrated cells are suspended in a buffered solution containing 0.1 m $CaCl_2$ and 0.01 m $RB_2CL$. The DNA is added to this solution and subjected to a heat pulse or shock, i.e., 37° C. for two minutes. The transformed cells are then chilled and may be transferred to a growth medium, whereby the transformed cells which produce cellobiose can be selected. The transformed cells were selected on minimal broth plates containing cellobiose and tetracycline (15 micrograms per milliliter). β-glucosidase activity was measured by following the hydrolysis of paranitrophenyl glucose (PNPG) at 395 NM in the spectrophotometer. The hydrolysis of 1 n mole of substrate produces a change of 0.013 in the optical density in a unit is defined as the release of 1 n mole per minute at 25° C.

The conversion of *E. coli* to cellobiose utilization was used as an assay to identify the β-glucosidase genes as follows. The total DNA was isolated from *E. adecarboxylata* and samples of DNA were digested separately to completion with the restriction endonucleases Eco RI, Pst I, Bam HI and Sal I. Several enzymes with 6 nucleotide recognition sites were used to reduce the chances of cutting the β-glucosidase gene and thus inactivating it. Each of these digests was then incubated under annealing conditions with the plasmid DNA pBR322 which had been cut with the same enzyme. pBR322 has single restriction endonuclease sites for RI, Sal, Bam and Pst. The annealed mixtures of the linear pBR322 DNA and the *E. adecarboxylata* DNA fragments were ligated with $T_4$ DNA ligase and were transformed into *E. coli* HB101. In the case of the Eco RI recombinants, the transformed *E. coli* were plated on medium containing cellobiose and tetracycline. Only those *E. coli* which received pBR322 could survive the tetracycline, and only those receiving the β-glucosidase gene could utilize the cellobiose and grow extensively on the medium. Within 4 days, a number of colonies were observed growing on the cellobiose containing plates. One of these colonies derived from the RI digest was isolated and further characterized. The isolate was strongly positive for β-glucosidase using the para-nitrophenyl β-glucosidase assay. The recombinant bacteria grew rapidly on cellobiose. The bacteria was grown up on cellobiose containing medium and the plasmid DNA was isolated from the culture.

The isolated plasmid DNA (P2 DNA) was digested with Eco RI, Bam HI, Sal and Pst and the resulting fragments were analyzed by electrophoresis on agarose gel and visualized by ethidium bromide staining. The plasmid contained a large (approx. 25 kb) insert of DNA at the RI site. The inserted DNA contained a single site for Sal I, 4 or 5 Bam HI sites and several Pst I sites. The P2 plasmid DNA which was digested with Sal I was used as a source of DNA to further refine the isolation of the β-glucosidase gene. The Sal I digest contained two fragments, one large and one smaller. As the original plasmid pBR322 contains only a single Sal I site, the insert must contain a second Sal I site to produce the two fragments. In addition, the inserted piece of DNA contains an RI site at each end, as it was derived from a complete RI digest. By digesting the P2 DNA first with Sal and then with RI, 4 fragments were obtained, each having an RI site at one end and a Sal site at the other. As a result, no one fragment could reanneal to form a circle by itself. One of the four fragments would be a 650 bp fragment from the original pBR322 which was part of the tetracycline gene; however, the ampicillin resistant gene remained intact. The double digest was allowed to reanneal, was ligated, and transformed into HB101, which was plated on cellobiose, ampicillin medium. Of a number of colonies, 55 were isolated and of these, 10 were further tested. Six of the 10 tested colonies were tetracycline sensitive and β-glucosidase positive, representing recombinations of the two insert fragments of P2.

One of the β-glucosidase positive, tetracycline sensitive colonies was chosen for restriction analysis of the plasmid DNA (designated P2-4). The DNA was isolated and digested with Bam HI and RI. When these digests were run out on agarose gels, it was clear that the inserted DNA in P2-4 contained at least two Bam HI sites as three fragments were observed. The RI digestion gave a single DNA species of approximately 14.5 kb or a size of 11 kb for the insert piece of DNA. The Bam digest was used without further digestion to refine the isolation of the β-glucosidase gene. The Bam HI digest was annealed and ligated and transformed into HB101. Of 10 colonies which were selected by growth on cellobiose, ampicillin medium, six were β-glucosidase positive. All six were grown up, plasmid DNA was isolated and digested with Bam HI. All six gave an identical pattern: a large 6.9 kb fragment and a smaller 2.2 kb fragment. A single colony was chosen for restriction analysis and was designated P2-4-10. Sal I, Pst I, or Eco RI digestion of the plasmid DNA of this colony gave a single 8.8 kb piece. The single Eco RI, Pst I and Sal I sites are all in the original pBR322. The β-glucosidase genes in the E. adecarboxylata genome lie within an approximately 5 kb Sal I - Eco RI piece and within a 2.2 kb Bam HI fragment within the Eco RI - Sal I piece. The gene probably contains no Bam HI, Eco RI, Sal I, or Pst I sites. All six isolates from the Bam HI digestion of P2410 contain the same two Bam HI fragments. The larger fragment (6.6 kb) includes the 3.7 kb Eco RI, Sal I piece of pBR322 which has the ampicillin resistant gene and the apparatus necessary for replication. The second smaller piece (2.2 kb) contains the β-glucosidase genes (if this insert fragment did not contain the β-glucosidase gene, one would expect some plasmids with the gene to lack this fragment and contain the other two smaller insert pieces.

In addition to the genetic material of *E. adecarboxylata,* the genetic material from other cellobiose utilizing organisms can be modified in a similar manner to be combined with a cloning vector and used to transform a microorganism incapable of utilizing cellobiose into one which is capable of utilizing cellobiose. This would be helpful where the microorganism to be modified is not closely related to the *E. adecarboxylata* and the formed plasmid from the *E. adecarboxylata* would be destroyed or inactivated upon transformation.

Preliminary Characterization of β-glucosidase

Expressed in *E. coli* β-Glucosidase in the intact cells.

HB101 carrying the recombinant plasmid P2410 grows rapidly in minimal broth with cellobiose (0.3%) as a carbon source. The doubling time of the culture is 66 minutes which compares well with the doubling time of HB101 in this medium with glucose as a carbon source (50-60 minutes). β-glucosidase activity can be readily assayed in the intact bacterial cells using the para-nitrophenyl glucose substrate. The cell-free culture fluid has no detectable β-glucosidase activity. All of the enzyme is cell-associated.

The rate of hydrolysis by the cells of PNPG is nearly linear for hours and continues until approximately 80% of the substrate is hydrolyzed. In the presence of an uncoupling reagent, sodium azide, even at relatively high concentrations (0.1%), the β-glucosidase activity of intact cells is not affected. These results indicate that in the intact cell, the β-glucosidase activity does not require energy produced by respiration. However, if cells are pretreated with arsenate for one hour prior to assay, the β-glucosidase activity is abolished. The activity is immediately restored in these cells by the addition of phosphate buffer. Clearly the enzyme activity depends upon phosphate and the arsenate inhibits the activity by acting as a phosphate analog. It is not clear whether the necessary phosphate is in a high energy form, but the cell appears to have considerable reserves of the material, as arsenate must be pre-incubated with the cells to be effective.

Proteins located in the periplasmic space of *E. coli* can be washed away by a cold shock procedure. In this cold shock procedure, the cells are subjected to osmotic shock by suspending the cells (1 g wet weight) in 80 ml of 20% sucrose - 0.03 M Tris-HCl, pH8, at about 24° C. to yield about $10^{10}$ cells per ml. This suspension was treated with disodium EDTA to give a concentration of $1 \times 10^{-3}$ M and mixed in a 1-liter flask on a rotary shaker (about 180 rpm). After 10 minutes, the mixture is centrifuged for 10 minutes at 13,000 × g in a cold room. The supernatant fluid is removed and the well-drained pellet is rapidly mixed with a volume of cold water equal to that of the original volume of the suspension. The suspension is next mixed in an ice bath on a rotary shaker for 10 minutes and centrifuged and the supernatant fluid is removed. The proteins are contained in this supernatant fluid. The β-glucosidase activity is not efficiently removed from the bacterial cells by cold shock. The enzyme is unlikely to be a periplasmic enzyme, nor does its activity depend upon other proteins easily removed from the periplasmic space. Such periplasmic proteins are involved in shock sensitive carbohydrate transport.

Toluene treatment of bacteria allows the measurement of cytoplasmic enzyme activities which are otherwise "cryptic" due to the surface membrane exclusion of the enzyme substrates. Such cytoplasmic activities as DNA polymerase and β-glucosidase can be measured in toluene treated *E. coli*. However, the β-glucosidase activity of HB101 (P2410) cells immediately and completely ceases upon addition of toluene to the medium. While there are a number of possible ways in which toluene could inhibit the activity, β-glucosidase is clearly not behaving like some other cytoplasmic enzymes. It is possible that this enzyme requires the bacterial membranes for its activity.

The β-glucosidase activity appears to be expressed constitutively in the host cell HB101. HB101 (P2410) cells were grown in medium without carbohydrates and were resuspended in minimal medium without carbohydrates. The β-glucosidase activity of the cells remained the same in the presence of added cellobiose as in its absence. The activity of cells grown in the absence of carbohydrate was close to that of cells grown on cellobiose. Addition of glucose to these cells had no immediate effect on the β-glucosidase activity. It is possible that the genes for β-glucosidase expression have been separated from regulatory genes by the molecular cloning procedures.

β-Glucosidase activity in bacterial lysates

It is possible to prepare a whole cell lysate of HB101 (P2410) which retains essentially all of the cellular β-glucosidase activity. The lysate is prepared by lysozyme digestion and sonication. The enzyme activity of the lysate requires $Mg^{++}$ ions and phosphate ions. The requirement for phosphate is surprising and indicates that the arsenate inhibition of β-glucosidase activity in the intact cell may not be due to loss of cellular energy production. It is possible that the enzyme may use phosphate in the cleavage of β-glucosides.

The crude bacterial extract is capable of converting cellobiose to glucose. In this experiment, the dialyzed extract was incubated with cellobiose in the presence of phosphate and magnesium. At intervals, samples were extracted, derivatized, and analyzed by gas chromatography. During the reaction, there was a linear decline in the amount of cellobiose and a proportionate increase in glucose. As this crude extract includes a large number of molecules which chromatograph at the position of phosphorylated sugars, it was not possible to determine whether the reaction provides via glucose-1-phosphate. Nevertheless, the crude extract is clearly able to hydrolyze cellobiose as well as PNPG at rates which are comparable (cellobiose: 0.12 nm/min; PNPG, 0.32 nm/min under identical conditions for the same extract).

The crude lysate is affected by the addition of detergent. At the level of 0.05%, Triton X-100 causes a 4-fold decrease in the β-glucosidase activity. Sodium cholate (0.1%) causes a similar inhibition. The effects of detergents on the lysate and of toluene on the intact cell indicate that β-glucosidase may be a membrane associated enzyme. To test this possibility, the crude sonicate was fractionated to separate the membrane vesicles from the free cytoplasmic material by centrifugation. After centrifugation, neither the membrane pellet, nor the supernatant fraction by themselves are particularly active. However, incubating the membrane fraction with an equal volume of the supernatant material restores 68% of the β-glucosidase activity of the initial sonicate. The supernatant material retains some of its ability to stimulate β-glucosidase activity even after brief boiling. The β-glucosidase activity of the membrane pellet appears to be stimulated by a relatively heat stable material present in the supernatant of an extensively dialyzed crude extract. This supernatant material seems to be "consumed" during the enzyme reaction. The addition of one volume of supernatant material allows the β-glucosidase reaction to proceed to a limited extent at a declining rate; further addition of supernatant restores the rate (temporarily) to linearity and allows the reaction to proceed further toward completion.

These formed plasmids of the present invention which include a cloning vector and a DNA fragment coding for cellobiose can be used to isolate genetic material which codes for the production of cellulase. The genetic material from a microorganism which is known to produce cellulase is isolated, randomly fragmented and these fragments are combined with the plasmids of the present invention. These newly formed plasmids are transformed into a recipient microorganism and tested. The original plasmids will include genetic material coding for specific characteristics such as tetracycline resistance as is the case with a plasmid formed from a cloning vector pBR322. The transformed microorganisms which are not destroyed by tetracycline are those which include the DNA material from the original plasmid including the genetic material coding for cellobiose production. By growing the microorganisms which are tetracycline resistant on cellulose, one will isolate those microorganisms which also include genetic material coding for the production of cellulase. The plasmids from these microorganisms can be isolated by known methods and transformed into other compatible microorganisms to confer the ability to produce cellulase. Since the original plasmids which were joined with the DNA material coding for production of cellulase are obviously well mapped, one can easily isolate the DNA material which codes for the production of cellulase. This DNA fragment can then be further trimmed down to eliminate DNA material which is not essential for production of cellulase and recombined with a cloning vector to be transformed into compatible microorganisms.

The formed plasmid P2410 is suitable for transformation into certain Pseudomonads to incorporate the ability to utilize cellobiose. Particularly one example is the transformation of *Zymomonas mobilis*. *Zymomonas mobilis* will ferment glucose, sucrose or fructose syrups at concentrations up to 20%, but will not utilize cellobiose. In order to produce a Zymonomas capable of utilizing the cellobiose utilization gene, the following procedures is followed:

The plasmid P2410 is spliced into plasmid RP1162 at the Eco RI sites. This sort of hybrid plasmid is known to be stable in Pseudomonads, including the cryophillic strains, as well as in *E. coli*. The hybrid plasmid is then transferred to HB101 and selected on ampicillin, streptomycin, and cellobiose as positive selection for the hybrid plasmid and can be mated into Zymomonas by a 3 strain cross of HB101 (P2410-RP1162). *E. coli* (RP4) and Zymomonas and the plasmid-carrying Zymomonas can be selected on minimal plates lacking the essential amino acids for HB101 growth (proline), plus ampicillin, streptomycin and cellobiose or glucose. The Zymomonas which grow on cellobiose should then be isolated.

Alternately, a cellobiase system can be cloned from a more closely related organism using the methods already employed in isolating P2410. This should not be necessary since most *coli* genes examined are well expressed in pseudomonads. However, if the P2410 plasmid is unable to confer cellobiose utilization on Zymomonas, the alternative of using a Pseudomonad gene as described above will yield the desired results. In this case, another cloning vector and/or mating system might prove superior to RP1162/RP4.

The Zymomonas modified to include the cellobiose utilization gene can then be cultured at desired conditions to grow on sources of cellobiose, glucose, sucrose or fructose or combinations of these and produce high concentrations of ethanol. Alternately, the modified Zymomonas can be grown on a solution of cellulose and cellulase. This can be accomplished by various methods.

For example, a second organism which produces cellulase can be added to a solution of cellulose and the modified Zymomonas. A second possible method is to simply add an exocellular cellulase to the cellulose. Such a source of cellulase is produced by the fungus *Trichoderma viride* QM 9414 discussed in Wilke et al, *Raw Material Evaluation and Process Development Studies for Conversion of Bromass to Sugars and Ethanol,* Biotechnology and Bioengineering, Vol. XXIII, pp. 163-183 (1981), incorporated herein by reference.

Alternately, the modified Zymomonas can be modified further by including a plasmid coding for the production of a cellulase. The organism *Cellvibrio vulgaris* (CV) includes DNA coding for production of cellulase.

There is a major problem in screening libraries of certain strains of Pseudomonad DNA in *E. coli* hosts. This is the problem of the instability of the Pseudomonad insert DNA in the plasmid vectors in *E. coli.* Briefly, the DNA of CV is excised from plasmid vectors in *E. coli,* but is maintained in lambda phage vectors. These results strongly indicate that while the Pseudomonad DNA can be maintained when actively selected for, without such selection pressure, the insert Pseudomonad DNA is frequently lost *without* loss of the plasmid vector in *E. coli* hosts. It is possible that the instability may be due to the large difference in GC content between the inserted DNA and the host cell DNA. To get around this difficulty, the ultimate host cell should be of a type closely related to the donor bacteria. Zymomonas should be used as the host for cloning CV DNA. However, because of the lack of a closely related pseudomonad which can be efficiently transformed, the *E. coli* strain HB101 should be used as the primary host.

Purified CV DNA is cut to approximately 20 kb sized pieces using a procedure to produce random fragments. The random nature of the fragments is extremely important and some care must be taken in the process. The restriction enzyme Hha I recognizes a 4-base sequence and gives a much more random digestion pattern than enzymes such as Eco RI which recognize 6 base sequences. The DNA is digested for various lengths of time, the digests pooled, and fractionated by sucrose gradient ultracentrifugation. The 15-20 kb sized fragments are combined and used for ligation to the plasmid DNA. This method of using fragments from digestions of differing extent tends to minimize problems which arise due to the resistance of some sites to cleavage of restriction enzymes.

The 20 kb Hha I cut CV DNA is then tailed with G residues using terminal transferase and annealed to Sal I cut hybrid plasmid RP1162-P2410 which has been tailed with C residues. Sal I does not cut RP1162, but cuts P2410 once in a nonessential region (the border between the pBR322 -position 650 - and the cellobiose utilization genes). The resulting plasmids are then transformed into *E. coli* HB101. Transformation levels in excess of $10^6$ per $\mu$g of recombinant DNA are routinely obtained using this host.

The HB101 cells are allowed to grow approximately 30 minutes in broth to allow replication and expression of the plasmids transferred into this host cell. These cells having the CV DNA material are then mixed with HB101(RP4) and Zymomonas in a three-way cross transformation to mobilize the recombinant plasmids at high efficiency from HB101 into Zymomonas. Because this transfer process is so efficient, (25-100% of the recipient cells receive plasmids) a small but very significant fraction of the bacteria which receive the unmodified plasmids do not destroy them despite restriction incompatibility. The overall efficiency of this process is only slightly below that of a one-step transformation process and results in the early transfer of the recombinant plasmid to a host cell in which the insert DNA will be stably maintained. The Zymomonas are then selected on minimal medium supplemented with streptomycin and ampicillin (to select for the plasmid) and cellobiose as the carbon source. The lack of proline eliminates the HB101 cells. The surviving cells are then tested as follows for the presence of cellulase genes.

With the cellobiase genes, there is no difficulty in obtaining a high level of expression of even a complex activity involving a membrane enzyme when genes from one bacteria are transformed to a related strain. The most critical aspect of any recombinant DNA experiment is the method used to identify the desired genes. First, a positive selection method to screen for Zymomonas carrying the CV cellulase genes is used. This approach requires a sufficiently high level of gene expression to permit Zymomonas to grow on cellulose. As an alternative method, a more lengthy screening procedure is outlined which will detect exceedingly small amounts of the enzyme, levels which might not permit growth.

Any selection which requires the Zymomonas to utilize cellulose should not require the bacteria to excrete the enzyme. Extracellular production of cellulase is a relatively rare phenomenon among bacteria and while the cellulase genes to be cloned are expressed as an extracellular enzyme by the donor organism (CV), it is possible that some specific mechanisms are involved in this process which are not cotransferred. The cellulase activity need not be an extracellular function in order to allow bacteria growth. *Cellvibrio vulgaris* produces the extracellular enzyme and is able to grow on cellodextrin (0.1%) agar plates. (Soluble cellodextrins of an average length of 11 glucose units were prepared by acid hydrolysis of paper and molecular sizing by ultra-filtration). CV grows very well in solution on the cellodextrin substrate. As a result, it is possible to enrich for cellulose-utilizing bacteria which do not excrete cellulase by growth in solution culture or to test individual colonies for growth in separate culture.

The colonies of Zymomonas which can grow on streptomycin, ampicillin and cellobiose contain the plasmid RP1162-P2410, along with any additional CV sequences. Several thousand colonies are washed off the plate surface, combined and allowed to grow on the cellodextrin broth for a one-week period. The cells are then diluted into fresh cellodextrin solution and allowed to grow up again. After several cycles of enrichment, aliquots of the solution are plated on cellobiose, antibiotic plates and 50 individual colonies are picked and tested for ability to grow and release color from dyed cellulose (CV actively grows at the expense of dyed cellulose). The requirement for serial enrichment and screening of a number of colonies is due to the frequency with which cellulolytic organisms cross-feed non-cellulolytic but cellobiose utilizing bacteria.

In order to confirm these results, one screens for the production of low levels of cellulase using a radioimmune assay. As this method lacks any growth selection step, the number of transformants and the background become matters of concern. It has been found that, using these methods of producing recombinants, a "background" of 500-1000 transformants per $\mu$g of restriction cut pBR322 is routinely obtained. That is, when pBR322 is cut with a restriction enzyme, treated with phosphatase and allowed to anneal and is ligated in the absence of foreign DNA, the pBR322 DNA gives 500-1000 transformants to drug resistance per $\mu$g. Intact pBR322 DNA gives about $10^6$ transformants per $\mu$g. Recombinant plasmid DNA gives 5,000-10,000 recombinants per $\mu$g, in the case of *E. adecarboxylata* DNA and pBR322. The background in this case was confirmed: approximately 11-12% of the transformants to ampicillin resistance remained tetracycline resistant when a Sal digest was inserted into the pBR322 Sal I site within the tetracycline gene.

A partial Hha I digest of CV DNA with an average size of 20 kb should be used. A complete genome equivalent of fragments of this size is approximately 100 fragments (2000 kb). This number is sufficiently low that a complete "library" of sequences is readily obtained from 1 $\mu$g of recombinant plasmid. The Hha I fragments are tailed with G residues and annealed with Sal I digested and C tailed pBR322 plasmid DNA. The Sal I site cuts the tetracycline resistance gene of this plasmid. By using the Sal I enzyme, background transformants are removed by screening for only those colonies which are ampicillin resistant but tetracycline sensitive. The recombinant plasmid DNA is then transformed into *E. coli* (HB101) followed by mobilization into Zymomonas. The recombinants should be selected on L-broth plates with ampicillin. About 400 of the ampicillin resistant, tetracycline sensitive recombinants are used and extracts screened for the production of cellulase by radioimmune assay. Each bacteria should be grown up in a separate 2 ml culture to avoid the problems of different growth rates of the bacteria. The cultures are then arrayed in a 20 row by 20 column square and 0.5 ml samples taken from each culture and pooled for each row (horizontal pools) and 0.5 ml from each culture pooled from each column (vertical pools). Each of the 40 pools should contain 20 ml of combined culture. The bacteria in these pools are then concentrated and extracts made by lysozyme treatment, sonication and addition of Triton X-100 (0.5%). These extracts are then assayed using the "F'(ab)2$_2$ well" method. This method is more cumbersome than blotting colonies with antibody bound to polyvinyl discs, but the well method has been more reliable under these conditions of use. These methods have been used in another context and have been able to detect $2 \times 10^8$ molecules of antigen, or less than one molecule per cell, in this case. In this assay, f'L(ab)2$_2$ fragments are produced from pepsin digestion of the anti-cellulase anti-serum and purified by passage over a protein A Sepharose column. The unbound material is allowed to adsorb to the walls of plastic microtiter dishes. The bacterial lysate is placed in the well. If the solution contains cellulase, it is bound to the wall by the f'(ab)2$_2$ fragment. The wells are then incubated with undigested antiserum followd by $^{125}$I-labeled-*S. aureus* protein A. The labeled protein A is bound only if the well contains the specific antigen because only in that case will the intact antibody be bound in the well. The wells are analyzed by autoradiography.

The recombinant bacteria which carry the cellulase are readily identified by the intersection of the positive column and row pools. By using a $20 \times 20$ assay, one can screen approximately 4 genome equivalents of DNA fragments.

When a recombinant plasmid which confers cellulose utilization upon Zymomonas is isolated, the followup procedures are relatively straightforward. First, trim down the size of the CV DNA by analysis of the restriction fragments so that the plasmid carries the minimum DNA to code for cellulose utilization. This can be a relatively time-consuming though straightforward occupation requiring the progressive mapping, cutting and stitching, and reselection of the genes. The objective is to have the active genes on small DNA fragments and a fairly detailed restriction map of the fragments.

As the host organism already produces enough cellulolytic activity for growth, the amount of genetic manipulation necessary to produce a useful organism may be time-consuming, but is not too difficult. Improved production of cellulolytic enzymes, modification of other aspects of the host's metabolism if required for integrated metabolism and a mechanism to maintain the plasmid in the bacteria in the absence of drug selection are some of the problems which might require attention.

Increased expression of the cellulase in Zymomonas can be engineered as follows.

The objective is to insert an efficient promoter near the gene and attempt to increase transcription. Ideally, this should be done in the Zymomonas host, but the lack of information on promoters in this system makes such an effort difficult. A better approach is to switch the plasmid into *E. coli*. Once the DNA which carries the cellulase genes has been pared down to a minimum size using the RIA test for expression in Zymomonas as a means of monitoring the presence of the gene, the DNA fragment will be joined to an "up" promoter (UV5) from the lactose operon on *E. coli*. This involves finding suitable restriction sites on the promoter DNA and the insert DNA or, if such sites are not easily available, the use of G and C tailing of the DNA fragments to allow their ligation. The resectioned DNA is placed into a suitable vector plasmid and transformed into *E. coli*. The location of the promoter is manipulated relative to the gene-carrying fragment to maximize the production of protein using the RIA to determine the amounts produced. Once a plasmid is constructed with an enhanced production of protein, the DNA with the new promoter is transferred back into Zymomonas on RP1162.

Thus, according to the methods of the present invention, a microorganism can be adapted to utilize cellobiose or, in the alternative, cellulose directly. In addition, the present invention provides an improved method of producing alcohol from cellulose. This substantially decreases the cost of the production.

Method of Production of Ethanol From Cellulose

The formed Zymomonas having the cellobiose utilization DNA from *E. adecarboxylata* and cellulose utilization DNA from CV is now capable of producing high concentrations of ethanol from cellulose. Cellulosic materials suitable for use would include wood, paper and agricultural crop residue just to name a few. The cellulosic material should be ground to about −10 mesh. The size reduction is not critical so long as the material will form aqueous suspensions which can be pumped, agitated and filtered.

The ground cellulosic material may be treated by acid hydrolysis to reduce some of the cellulose to simpler sugars. This will permit the bacteria to consume both glucose and cellulose. In the acid hydrolysis treatment, the ground cellulosic material is mixed with about 0.09M $H_2SO_4$ and heated. This can be continued until the desired degree of breakdown of cellulose is attained. Increasing the temperature or time will inrease the breakdown of the cellulose.

After acid hydrolysis, the acid cellulose mixture should be neutralized. The neutralized aqueous cellulosic mixture is then subjected to fermentation using the modified Zymomonas of the present invention. If the cellulosic material is not subjected to acid hydrolysis, the ground cellulosic material should be mixed with water to produce an aqueous slurry prior to fermentation.

The fermentation can be conducted in a batch or continuous reactor. Generally, to ferment the cellulose in the aqueous slurry, the modified Zymomonas of the present invention is mixed with the slurry and agitated. A temperature of about 35° C. should be maintained during the fermentation. The cell concentration will vary as the reaction occurs, but a cell concentration of 50 g dry wt/liter is normally acceptable.

During this fermentation process, the bacteria breaks down the cellulose to cellobiose. The bacteria then proceeds to produce ethanol while consuming the cellobiose. The bacteria used in the fermentation process should preferably be recycled. Therefore, the fermentation should be discontinued before ethanol concentration exceeds the tolerance of the bacteria (i.e., about 6–10%). Although the bacteria of the present invention should exhibit better ethanol tolerance than any other cellulose consuming bacteria, the ethanol concentration will increase until that tolerance is exceeded and the bacteria destroyed. Accordingly, the bacteria should be removed when the ethanol level reaches about 6–10%.

To remove the bacteria, fermented liquid is filtered to remove the undigested cellulose. The filtrate is subjected to centrifugation. The bacteria will then form a solid pellet which can be easily separated from the liquid.

An alternate method of producing ethanol according to the present invention is to add cellulase produced by a separate organism which breaks down the cellulose to cellobiose and adding Zymomonas modified with the plasmid coding for the production of cellobiose to the cellulose-cellulase mixture. This is then fermented according to the above procedure.

Having disclosed our invention, we claim:

1. A recombination DNA plasmid comprising a cloning vector having covalently bound thereto a DNA insert coding for the production of beta-glucosidase wherein said DNA insert coding for the production of beta-glucosidase is isolated from *Esherichia adecarboxylata*.

2. *Esherichia coli* comprising a recombinant DNA cloning vector having covalently bound thereto a DNA insert coding for the production of beta-glucosidase, said DNA insert isolated from *Esherichia adecarboxylata*.

* * * * *

UNITED STATES PATENT AND TRADEMARK OFFICE
CERTIFICATE OF CORRECTION

PATENT NO. : 4,464,471
DATED : August 7, 1984
INVENTOR(S) : Richard W. Armentrout; Ronald D. Brown It is certified that error appears in the above-identified patent and that said Letters Patent is hereby corrected as shown below:

Column 4, line 23    "$M_b^-$" should be --$M^-_b$--.

Column 11, line 64    "$F'(ab)2_2$" should be --$F'(ab)_2$--.

Column 12, line 3    "$f'L(ab)2_2$" should be --$f'(ab)_2$--.

Column 12, line 9    "$f'(ab)2_2$" should be --$f'(ab)_2$--.

Signed and Sealed this

Seventh Day of May 1985

[SEAL]

Attest:

DONALD J. QUIGG

Attesting Officer      Acting Commissioner of Patents and Trademarks